United States Patent [19]

Toomey, Jr.

[11] Patent Number: 4,482,437

[45] Date of Patent: Nov. 13, 1984

[54] ELECTROCHEMICAL REDUCTIONS OF CYANOPYRIDINE BASES

[75] Inventor: Joseph E. Toomey, Jr., Indianapolis, Ind.

[73] Assignee: Reilly Tar & Chemical Corp., Indianapolis, Ind.

[21] Appl. No.: 597,013

[22] Filed: Apr. 5, 1984

[51] Int. Cl.$^3$ ............................................. C25B 3/00
[52] U.S. Cl. .................................. 204/74; 204/59 R
[58] Field of Search ................................ 204/74, 59 R

[56] References Cited

PUBLICATIONS

Krishman et al., *J. Electroanal. Chem. Interfacial Electrochem.*, 88 (30), 433 (1978).
Volke et al., *Coll. Czech. Chem. Commun.*, 33 (8), 2560 (1968).
Volke et al., *Coll. Czech. Chem. Commun.* 27, 1597 (1963).

*Primary Examiner*—John F. Niebling
*Attorney, Agent, or Firm*—Woodard, Weikart, Emhardt & Naughton

[57] ABSTRACT

Improved electrochemical reductions of cyanopyridine bases in which the reduction is performed by electrolysis in an ion-exchange membrane-divided flow cell at a lead dioxide cathode and in an aqueous or partly aqueous medium comprising sulfuric acid in at least a 1:1 mole ratio with the cyanopyridine base. In the case of 2- and 3- isomers, an iron salt is also added to the catholyte as a catalyst. In the case of the 4- isomer, an efficient, semi-continuous batch process is reported. With all bases, significant advantages of a commercial and industrial nature are reported over prior art static, beaker cell technology.

9 Claims, No Drawings

ELECTROCHEMICAL REDUCTIONS OF CYANOPYRIDINE BASES

BACKGROUND OF THE INVENTION

This invention relates generally to the field of pyridine chemistry with particular application in providing improved electrochemical processes for the reduction of cyanopyridine bases in commercially practicable flow cells.

Much attention has focused over the years on the reduction of nitriles, which are organic compounds containing the cyano radical "—CN." to their corresponding amines. The field of pyridine chemistry has been no less attentive than others in this regard, with the products of such reduced cyanopyridines, or pyridine carbonitriles as they are also called, exhibiting valuable uses in such applications as carbon dioxide scavengers, corrosion inhibitors, chelating agents, and others.

Historically, three approaches have been used to reduce these nitriles to their corresponding amines, those being catalytic hydrogenations, chemical reducing agents, and electrochemical reductions. In this regard, the ideal approach would be one that produces high yields of the primary amine using an inexpensive reducing agent, low temperatures, and not involving heavy demands on or uses of pollution control procedures. Reported successes approaching this ideal have been few, however, as the production of primary amines in good yields is often hampered by a pair of side reactions which occur during reduction. The first of these leads to the corresponding secondary amine as reported in H. Rupe, E. Hodel, Helv. Chim. Acta, 6, 865 (1923) and H. Rupe, W. Brentano, ibid., 19, 588 (1936). The second leads to hydrogenolysis of the amine to form the less-desired hydrocarbon as reported in J. Corse. J. T. Bryant, H. A. Shoule, J. Am. Chem. Soc., 68, 1907 (1946) and N. J. LeoSnard, G. W. Leubner, E. H. Burk., J. Org. Chem., 25, 982 (1960).

Catalytic hydrogenation procedures have suffered from both of these side reactions in addition to requiring undesirable elevated temperatures in most instances which promote thermal reacting leading to unwanted products and tars. In order to obtain satisfactory yields of primary amine, for example, trapping of the amine by an acetylating agent [F. E. Gould, G. S. Johnson, A. F. Ferris, J. Org. Chem., 25, 1658 (1960)]or the use of large quantities of ammonia [M. Rabinovitz in "The Chemistry of Functional Groups: The Chemistry of the Cyano Group" S. Patai, Ed, Interscience. N.Y. 1970, p. 321] has been required.

Active metal-reducing agents such as sodium in an alcohol solvent have also been reported, but once again with many accompanying problems [E. Bamberger, Ber., 20, 1703, 174 (1887)] which have prevented such methods from gaining general acceptance. Similarly, hydride-reducing agents have been reported to usually work well [N. C. Gaylord, "Reduction with Complex Metal Hydrides," Interscience, N.J., 1956 and S. Yamada, Y. Kikugawa, Chem. Ind. (London), 1967, 1325W , but require the use of an expensive reducing agent. For that reason, such hydrides have been used only in special cases where the value of the product can support a high-selling price. In addition, the strongly basic nature of hydrides can initiate unwanted side reactions which have been a further complicating factor.

Some electrochemical procedures which have been reported seem to fulfill many of the desired features of an ideal nitrile reduction since low temperatures can be used, the electron is a very inexpensive reducing agent, and such methods normally do not place high demands on pollution controls. In the case of cyanopyridines, also referred to as pyridine carbonitriles, there have been many analytical studies particularly of the three isomeric monocarbonitriles.

For instance, L. P. Krasnomolova, A. E. Lyuts, V. I. Artyukhin, O. V. Agashkin, D. Kh. SembaeV, B. V Suvorov, Zh. Fiz. Khim., 52, 85 (1978) correlated the ease of reduction of such compounds at a mercury cathode with both the position of the long wave length ultraviolet adsorption band and the nitrile stretching frequencies in the infrared spectroscopy. Rafik O. Loutfy, Raouf O. Loutfy, Can. J. Chem., 51, 1169 (1973) also correlated ease of reduction with the $n,\pi^*$-triplet energies. The polarographic behavior of cyanopyridines has also been extensively studied and the mechanistic implications reported [J. Volke, R. Kubicek, F. Santavy, Coll. Czech. Chem. Commun., 25, 1510 (1960); V. A. Serazetdinova, B. V. Suvorov, O. A. Songina, Izv. Akad. Nauk Kaz. SSR, Ser. Khim., 18 (3), 64 (1968); V. A. Serazetdinova, B. V. Suvorov, O. A. Songina, Khim. Geterotsikl Soedin, (3), 327 (1973); V. A. Sarazetdinova, B. V. Suvorov, Nov. Polyarogr. Tezisy Kodl. Vses. Soveshch. Polyarogr., 6th, J. Stradino. ed., Zinatne, Riga, USSR 1975, p. 157; A. M. Kardos, P. Valenta, J. Volke, J. Electroanal. Chem., 12, 84 (1966); A. Kitani, K. Iida, K. Sasaki, Denki Kagaku, 41 (12), 900 (1973); J. Volke, V. Skala, J. Electroanal. Chem. Interfacial Electrochem., 36 (2), 383 (1972)].

However, there has been much less work reported on the preparative scale synthesis of these cyanopyridines by electrochemical means. For example, V. Krishman, K. Raghupathy, H. V. K. Vdupa, J. Electroanal. Chem. Interfacial Electrochem., 88 (30), 433 (1978) reported the successful reduction of 3-cyanopyridine in aqueous hydrochloric acid at a cathode having a palladium black deposit on a carbon base. The cell design in this case was a rudimentary beaker-type cell with a ceramic diaphragm thus having little or no commercial significance. The reported yield was good at about 80%, but current efficiency was moderate (about 40%). To achieve these results, however, the authors reported having to maintain the current density at less than or equal to about 20 mA/cm$^2$, with higher densities resulting in poor yields and efficiencies.

Similarly, J. Volke, A. M. Kardos, Coll. Czech. Chem. Commun., 33 (8), 2560 (1968) reported reductions of all three isomeric mononitriles of pyridine under impractical conditions, with both the 2- and 4- isomers reportedly giving adequate results. In the case of 3-cyanopyridine, anomolous results were obtained. With all such experiments, however, Volke used very dilute solutions (10 mM) in a phosphate buffer at a mercury cathode, and in a standard beaker cell design. Also, product isolation was not done in this work, but yields were assessed analytically with Ninhydrin reagent. A cohesive mechanistic scheme was reported to account for the pH dependence and polarization behavior [J. Volke, V. Skala, J. Electroanal. Chem. Interfacial Electrochem. 36 (2), 383 (1972); J. Volke A. M. Kardos, Coll. Czech. Chem. Commun., 33 (8), 2560 (1968)]. Interestingly, there also seems to be some variance between V. Krishman, K. Raghupathy, H. V. K. Vdupa, J. Electroanal. Chem. Interfacial Electrochem., 88 (30), 433 (1978), which reported a synthetically useful reduction of 3- cyanopyridine, and others [A. M. Kardos, P. Valenta, J. Volke, *J. Electroanal. Chem.*, 12, 84 (1966); J. Volke, R. Kubicek, F. Santavy, *Coll. Czech. Chem. Commun.*, 25, 1510 (1960): J. Volke, A. M. Kardos, *Coll. Czech. Chem. Commun.*, 33 (8), 2560 (1968)] which report polarographic results supporting nitrile cleavage instead of nitrile reduction. Thus, the correlation of results at very dilute and higher (more practical) concentrations is not good and the analytical reports do not accurately reflect synthetic scale results. In addition, Volke and Holubek [*Coll. Czech. Chem. Commun.*, 27, 1597 (1963)] reported a spectroscopic identification of the product of 4-cyanopyridine reduction; however, the yield was not disclosed as a special apparatus was used and very small amounts of product were produced.

The synthetic work of the above references reporting electro-reductions of cyanopyridine isomers suffers from many common disadvantages. For example, only 3-cyanopyridine has been successfully reported to be reduced in kilogram-size quantities, the other isomers being reduced only in very small amounts [V. Krishman, K. Raghupathy, H. V. K. Vdupa, *J. Electroanal. Chem. Interfacial Electrochem.*, 88 (30), 433 (1978)]. Even this large-scale reduction of 3-cyanopyridine, however, was done in aqueous hydrochloric acid which is corrosive, and required a specially prepared noble metal cathode which is expensive to produce. In this regard, mercury is the only other reported cathode material besides palladium o carbon.

Furthermore, all of this prior work has been performed in beaker cell designs which are acceptable for bench scale (0.01-1 Kg) and analytical experiments. but have no economic value for commercially practicable productions. There is no teaching or suggestion in any reference to applicant's knowledge that such electrochemical reductions of cyanopyridine bases have been or can be performed, or even attempted, using other cell geometries and techniques which may have commercial potential. There are three other references which bear on nitrile reduction, but provide very little, if anything, over the references already discussed [*H. Lund, Acta Chem. Scand.*, 17 (8), 2325 (1963); M. Lacan, I. Tabakovic, J. Hranilovic, Z. Vajtner, R. Hranilovic, *Croatica Chem. Acta*, 44, 385 (1972); M. Lacan, et al., ibid, 43, 229 (1971)].

SUMMARY OF THE INVENTION

Applicant's present invention corrects these deficiencies previously experienced in the art, and in so doing proves for the first time the viability of conducting electrochemical reductions of cyanopyridine bases in commercially practicable flow cells. In so doing, applicant's reductions were done at planar and high-surface area cathodes, preferably of lead or lead alloys, and without the necessity of highly-corrosive electrolytes, to successfully achieve large-scale syntheses of the corresponding primary amines in batch, semi-continuous or continuous processes. Applicant's preferred flow cells are not restricted as to particular design geometries, with factors such as electrolyzer feed rate and preparation, product isolation, user need and the like governing the particular design and processing used.

In applicant's preferred electrochemical reduction of 2- and 3-cyanopyridines, and their substituted bases as described and depicted in detail hereinbelow, all of these above advantages have been achieved in addition to obtaining high yields at improved current efficiencies. Lead and alloyed lead cathodes have been preferred, as has an aqueous or partly aqueous electrolyte which comprises sulfuric acid in at least about a 1:1 mole ratio with the selected base. Applicant has also discovered that the presence of at least a catalytic amount of iron, preferably as a salt, in the electrolyte greatly improves process efficiency in yielding the corresponding primary amines by inhibiting the formation of unwanted byproducts which otherwise would reduce yields and be troublesome in whatever isolation method is employed.

In the case of applicant's preferred reduction of 4-cyanopyridines, a semi-continuous process has been used which allows isolation of the desired end product as a sulfuric acid salt accompanied by regeneration and recycling of the nonspent electrolyte solution. Applicant's reductions have preferably been done at a high-surface area lead cathode in a filter press flow cell, and has achieved many advantages in contrast to existing methods both in economy of processing and in technology associated with processing and product isolation, as further described hereinbelow.

Related objects and advantages of the present invention will be apparent from the following description.

DESCRIPTION OF THE PREFERRED EMBODIMENTS

For the purposes of promoting an understanding of the principles of the invention, reference will now be made to the embodiments and specific language will be used to describe the same. It will nevertheless be understood that no limitation of the scope of the invention is thereby intended, such alterations and further modifications in the device, and such further applications of the principles of the invention as illustrated therein being contemplated as would normally occur to one skilled in the art to which the invention relates.

In accordance with the above summary, applicant has discovered and proven in one preferred embodiment of his resent invention that electrochemical reductions of 2- and 3-cyanopyridines having the formula

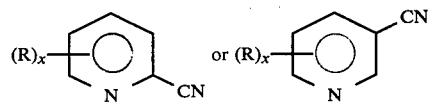

wherein:
x=0-2;
R=an alkyl group having about 1-6 carbon atoms, —(CH$_2$)$_n$—aryl where n=0-3, —CN, —CO$_2$R' where R'=H or an alkyl, aryl or aralkyl group having about 1-10 carbon atoms, or —CONR"R'" where R" and R'" can be selected from the group consisting of H, an alkyl group having about 1-6 carbon atoms, and wherein R" and R'" taken together may be part of a heterocyclic ring,
and wherein two adjacent R groups on the ring taken together may be a fused cycloalkyl or a fused aryl group, are successfully performed in a flow cell having definite commercial and industrial applications. Applicant's preferred reductions have taken place at a lead or alloyed lead cathode in a filter press flow cell equipped with ion-exchange membrane divider in contrast to the ceramic diaphragms used in the past. An aqueous or partly aqueous electrolyte has been preferred comprising sulfuric acid in at least a 1:1 mole ratio with the cyanopyridine base present in the medium. Also preferred has been the discovery that the presence of at least a catalytic amount of iron, most preferably as an iron salt, in the medium greatly enhances the yield, current efficiency and other advantages of applicant's process when the carbonitrile is in the 2- or 3-position of the ring. This is accomplished at least in part by inhibiting the formation of unwanted byproducts of the reaction which have plagued prior art processes as described in the background section of this application.

As used in this application, the phrase "electrochemical reduction" is meant to include all possible variations as to reaction conditions and the like which are known to those of ordinary skill in the art to which applicant's invention pertains. The only exceptions to this relate to any specific conditions or features which have shown to be required from applicant's testing to date which are further detailed hereinbelow. In addition, the phrase "flow cell" is meant to be restrictive only in the sense of excluding any cell consisting of a tank, beaker or container of similar function which is employed as a mixed or unmixed electrolyzer and which is limited by the inability to achieve a substantially plug flow of electrolyte in the reactor, by the inability to obtain a high space-time yield consistent with more sophisticated electrolyzers, or by the inability to effectively use ion-exchange membranes which are most often conveniently made and purchased in sheet form. In so doing, the phrase "flow cell" is meant to include all other electrolyzers which may employ either a batch or continuous mode of operation with a substantially plug flow of solution through the reactor and which can be conveniently constructed as filter-press, disc-stack, or concentric tube cells. For example, this includes both batch reactors where the electrolyte is continually recirculated through the closed loop as well as continuous processes where steady-state conditions are approached and/or product is continually removed and the electrolyte regenerated for further use. No cell geometries are excluded from the scope and intent of applicant's invention so long as they comply with these fluid-flow characteristics.

With each particular nitrile, the choice of reactor and operational mode for use with applicant's invention varies with the particular chemistry involved, both as to reaction conditions which must be observed as well as other factors affecting product separation, purification, and the like. Applicant's preferred electrochemical flow cell to date is his own filter press cell which is the subject of U.S. patent application, Ser. No. 477,529, filed Mar. 21, 1983 and entitled FILTER PRESS ELECTROCHEMICAL CELL WITH IMPROVED FLUID DISTRIBUTION SYSTEM. Accordingly, this prior application is hereby incorporated herein by reference in its entirety as to all pertinent and relevant aspects thereof relating to prior cell design technology and to the disclosure and understanding of applicant's preferred flow cell as used herein.

As to specific materials or conditions, applicant's preferred electro-reductions to date have used a cathode made of lead alone or alloyed with and possibly supported on such materials as antimony and/or silver, cadmium, titanium, or carbon. As stated earlier, an aqueous or partly aqueous electrolyte solution has been preferred comprising sulfuric acid in at least a 1:1 mole ratio with the cyanopyridine precursor in solution. An amount of a lower alcohol or acetonitrile has also been mixed with water in this medium at least in certain experiments to date. An ion-exchange membrane divider has also been used in all cases, in contrast to the porous, nonselective dividers previously employed.

As to specific conditions of applicant's reactions to date, preferred temperatures have ranged between about 0°–90° C., with about 25°–50° C. being most preferred. Preferred current densities have ranged between about 0.1–100 $mA/cm^2$, with about 5–25 $mA/cm^2$ being most preferred. As to the electrolyte itself, cyanopyridine concentrations have preferably been maintained between about 0.5–35 wt %, while most preferred has been a range of about 10–20 wt % in solution. Concentrations of the iron salt catalyst in the medium have been as low as 1 ppm up to the solubility limit of the salt with enhanced results being obtained. Most preferred, however, has been the addition of iron sulfate to a partly or wholly aqueous system so as to achieve an end concentration from about 5 ppm up to the solubility limit in solution. The preferred anolyte has been prepared from sulfuric acid and water in quantities similar to that being used in the particular catholyte employed for the reaction; but there are cases when such anolyte composition deviated from that used for the catholyte, particularly when large volume changes were encountered during the electrolysis.

In a second preferred embodiment of applicant's present invention, 4-cyanopyridine has been proven to reduce in an effective process which allowed semi-continuous isolation of product as a sulfuric acid salt and regeneration and reuse of the electrolyte solution. Alternately, the carbonate salt could also be isolated but recycling of the electrolyte was not possible. In this regard, these reductions can be performed essentially the same as with the 2- and 3-isomers with the yield and current efficiencies being higher at about 90% and 80%, respectively. The weights by part of electrolyte in this case were 4-cyanopyridine (1), sulfuric acid (1.5) and water (1.2). Alternately, also preferred has been a semi-continuous process comprising reducing 4-cyanopyridine in an aqueous sulfuric acid media with a lower alcohol cosolvent (preferably methanol) until the conversion reaches about 40–80%, with about 50–60% being preferred. At that point, applicant's preferred process has proceeded by adding sufficient 4-cyanopyridine to account for that consumed, cooling the electrolyte to precipitate 4-picolylamine as the sulfate salt, filtering the same to collect this product, and then recycling the filtrate to the electrochemical flow cells with the addition of sufficient sulfuric acid to account for that lost in the product salt. In so doing, the applicant has shown the catholyte can be recycled more than six times with little or no loss in process performance. The most preferred weights by part in this embodiment has been 4-cyanopyridine (1), sulfuric acid (1.4), water (1.7), and methanol (1.1).

Unlike the case of applicant's work with the 2- and 3-cyanopyridine bases, however, the testing to date has shown that electrochemical reduction of 4-cyanopyridine bases is not enhanced, and the isolation of the acid salt of the product is in fact detrimentally affected, by the presence of any amount of iron catalyst as described above.

In addition to those individual advantages mentioned above, general benefits have been found to exist with applicant's preferred flow cell arrangements and processes as described in this application. These features include such things as the ability to continually remove heat from the flow cell as, for example, by circulating the electrolyte through a heat exchanger or similar apparatus during the process. Continual product removal and regeneration of the electrolyte is also possible, as described above, using standard and accepted known to those of ordinary skill in the art with regard to the particular reaction involved. Specific electroreductions have also proven to be at least equally efficient as prior art reports, and have the benefit of being able to use high-surface area (HSA) cathodes at which the reduction takes place. Examples of such HSA electrodes are wire meshes, metal particles such as lead spheres or other packing material, as well as those discussed in more detail in applicant's electrochemical cell application previously incorporated herein by reference.

Reference will now be made to specific examples for the purpose of further describing and understanding the features of applicant's preferred embodiments as well as their advantages and improvements over the art. In this regard, where possible, specific reference has been made in the examples to known prior art processes in order to better understand and distinguish applicant's invention herein. It is further understood that these examples are representative only, and that such additional embodiments and improvements of the same are within the contemplation and scope of applicant's invention as would occur to someone of ordinary skill in this art.

EXAMPLE 1

2-Picolylamine

A flow cell having a cation-exchange membrane and a lead cathode consistent with that disclosed in U.S. patent application Ser. No. 477,529 was used. A catholyte was prepared from the following weight parts: 2-cyanopyridine (1.0), sulfuric acid (2.6), water (1.9), $Fe_2(SO_4)_3$ (0.01). The anolyte used was dilute sulfuric acid. Charge was passed through the cell until >95% conversion of the cyanopyridine was achieved. Analysis by spectroscopic means indicated a 91% yield and 5% current efficiency had been obtained. An identical reduction without added iron salts gave an 18% yield by similar analysis. Additional experiments were also conducted using other cathode materials such as mercury, lead amalgams or other lead alloys, copper, silver, cadmium and carbon, with similar success. Organic cosolvents and other strong acids were used in these additional experiments and were also found to be acceptable.

EXAMPLE 2

3-Picolylamine

The procedure in Example 1 was used except for substituting 3-cyanopyridine for the 2-isomer. The yield was 55% at 75% current efficiency. When the iron salts were left out, only a 15% yield was realized.

EXAMPLE 3

Reduction of the 3,5-Dicyanopyridine

The procedure in Example 1 was used by appropriately substituting the dinitrile for the mononitrile. Two reduction products were observed in 55% combined yield at 6F/mole charge, those being 5-aminomethylnicotinonitrile and 3,5-(bis-aminomethyl)pyridine. The relative ratio of these products and the total yield were found to change when the quantity of charge passed through the cell was varied.

EXAMPLE 4

5-Methyl-3-picolylamine

The procedure in Example 1 was used except with 5-methylnicotinonitrile. At 5F/mole charge passed, a 60% yield of 5-methyl-3-picolylamine was observed.

EXAMPLE 5

6-Aminomethylpicolinamide

Substituting 6-cyanopicolinamide for the mononitrile in the procedure of Example 1 gave a 45% yield of 6-aminomethylpicolinamide at 4F/mole charge passed.

EXAMPLE 6

4-Picolylamine

The catholyte consisted of the following weight parts: 4-cyanopyridine (1), sulfuric acid (1.5), and water (0.5). The anolyte was 30 wt % sulfuric acid. The flow cell used had a cation-exchange membrane and lead cathode consistent with that disclosed in U.S. patent application Ser. No. 477,529. Charge was passed at 5 $mA/cm^2$ until 4F/mole at 25° C. The catholyte was neutralized under a stream of $CO_2$ with NaOH until phase separation occurred. The layers were separated and the organic layer concentrated in volume until the greater part of the water was removed. Addition of acetone to the concentrate gave white needles of the amine carbonate which were filtered off, washed with fresh acetone and dried to give a 92% yield of solid, mp 235°-245° C. dec.; nmr spectrum ($D_2O$, ppm) 4.03 (S,2) 4.57 (S,2) 7.09 (d, 2), 8.16 (d,2); ir (nujol mull, $cm^{-1}$) 3300, 3200, 3100, 2940, 2870, 1608, 1518, 1500, 1470, 1420, 1390, 1350, 1315, 1270, 1247, 1228, 1172, 1073, 1045, 1013, 932, 902, 830, 811, 725, 687, 653.

Alternately, the catholyte could be neutralized with sodium hydroxide alone and the organic materials extracted, separated, and concentrated. Vacuum disillation gave a 96% yield of 4-picolylamine.

Organic cosolvents could be used with the aqueous electrolyte and, when methanol was used, a semi-continuous isolation method resulted. In this case, the catholyte consisted of 4-cyanopyridine (1) ACS reagent-grade sulfuric acid (1.5), water (1.8), and methanol (1). The anolyte was 30 wt % sulfuric acid. The methodology used for reduction was the same as above except that only 2F/mole of charge was passed. An additional amount of 4-cyanopyridine (0.5 was added, stirred until all the cyanopyridine dissolved, cooled to 0° C. and the product 4-picolylamine sulfate salt filtered to obtain about a 50% isolated yield. To the filtrate was added sufficient sulfuric acid to account for that lost in the product salt and the electrolyte was reduced once again (2F/mole). Repeating the addition of cyanopyridine, cooling, isolation of product salt, and addition of sulfuric acid produced a 98% yield of isolated salt. The cyclic operation could be continued past 6 cycles with greater than a 93% total isolated yield and 100% current efficiency.

EXAMPLE 7

Reduction of 2-Cyano-4-phenylpyridine

The method of Example 1 was used for 2-cyano-4-phenylpyridine to give a 93% yield of 4-phenyl-2-pyridinemethanamine. Neutralization of the catholyte and extraction followed by stripping of the extracting solvent (MIBC, for instance) gave a crude yield of 86% by GC analysis.

EXAMPLE 8

Reduction of 2-Cyano-4-carbomethoxypyridine

The method of Example 7 was used to obtain a crude yield of 72% 4-carbomethoxy-2-pyridinemethanamine at 3.5 F/mole. Increasing the charge passed beyond 4F/mole resulted in lowered yields of the above-mentioned product.

EXAMPLE 9

Reduction of 2-Cyanoquinoline

Using the method of Example 1 gave an 88% yield of 2-quinolinemethanamine by spectroscopic analysis at 4F/mole. Increasing charge passed decreased the yield.

EXAMPLE 10

Reduction of 4-Cyano-2-methyloyridine

The first-described method of Example 6 was used with isolation by distillation. The spectroscopic properties of the product were consistent with 2-methyl-4-pyridinemethanamine (81% yield): nmr ($D_2O$, ppm) 3.55 (S, 3), 3.96 (S,2 ), 4.61 S,2), 7.0–8.1 (m,3); ir (nujol mull, $cm^{-1}$) 3000–3300, 1515, 1475.

I claim:

1. In a electrochemical reduction of a 2- or 3-cyanopyridine base having the formula

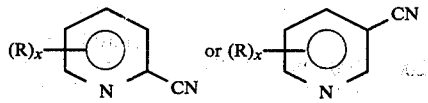

wherein:

x=0–2;

R=an alkyl group having about 1–6 carbon atoms, $-(CH_2)_n$-aryl where n=0–3, $-CN$, $-CO_2R'$ where $R'=H$ or an alkyl, aryl or aralkyl group having about 1–10 carbon atoms, or $-CONR''R'''$ where R'' and R''' can be selected from the group consisting of H, an alkyl group having about 1–6 carbon atoms, and wherein R'' and R''' taken together may be part of a heterocyclic ring, and wherein two adjacent R groups on the ring taken together may be a fused cycloalkyl or fused aryl group, the improvement comprising the step of conducting the electro-reduction reaction at a lead or alloyed lead cathode in a flow cell having an ion-exchange membrane divider, said conducting further being in an aqueous medium comprising sulfuric acid in at least a 1:1 mole ratio with the base in solution and further containing at least a catalytic amount of an iron salt.

2. The electro-reduction reaction in claim 1 in which the improvement additionally comprises the step of adding an amount of iron salt or suitable precursor to the medium sufficient to produce a concentration of iron salt above about 5 ppm in the electrolyte solution.

3. The electro-reduction reaction in claim 2 in which the improvement additionally comprises the step of maintaining the temperature of the electrolyte between about 25°–50° C. and the current density between about 0.1–100 $mA/cm^2$ during said conducting.

4. The electro-reduction reaction in claim 3 in which the catalyst is an iron sulfate salt.

5. The electro-reduction reaction in claim 4 in which the base is 2-cyanopyridine.

6. The electro-reduction reaction in claim 4 in which the base is 3-cyanopyridine.

7. The electro-reduction reaction in claim 1 in which the improvement additionally comprises the step of adding an iron salt catalyst or suitable precursor to the electrolyte solution circulating through the flow cell sufficient to increase yield by at least about 20% of a product expected in the reaction, as a percent of total product obtained.

8. The electro-reduction reaction in claim 2 in which said adding is in addition to any autogenous amount of iron salt generated in situ from the sulfuric acid used in the electrolyte solution.

9. An improved electrochemical reduction reaction, comprising the steps of:
   (a) combining an amount 4-cyanopyridine and at least a slight stoicheometric excess of sulfuric acid in a methanolic aqueous medium;
   (b) charging this solution into the catholyte compartment of a flow cell having a lead or alloyed lead cathode and ion-exchange membrane divider;
   (c) charging the anolyte compartment of the cell with dilute sulfuric acid;
   (d) conducting electrolysis in the cell until about 50–60% conversion of the 4-cyanopyridine base has been achieved;
   (e) adding an amount of 4-cyanopyridine to the catholyte after said conducting to account for part or all of the nitrile consumed and thereby precipitating out the product as a sulfuric acid salt;
   (f) filtering out the precipitated product and recycling the remaining filtrate after the addition of sulfuric acid to account for that lost in the product salt.

* * * * *